United States Patent
Tamura et al.

(10) Patent No.: US 7,508,518 B2
(45) Date of Patent: Mar. 24, 2009

(54) PARTICLE MEASURING METHOD AND PARTICLE MEASURING APPARATUS

(75) Inventors: Akitake Tamura, Nirasaki (JP); Kaoru Fujihara, Nirasaki (JP); Teruyuki Hayashi, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 12/078,172

(22) Filed: Mar. 27, 2008

(65) Prior Publication Data

US 2008/0239283 A1 Oct. 2, 2008

(30) Foreign Application Priority Data

Mar. 28, 2007 (JP) .............................. 2007-085561

(51) Int. Cl.
*G01N 21/00* (2006.01)
*G01N 21/55* (2006.01)

(52) U.S. Cl. ..................... 356/432; 356/441; 356/445

(58) Field of Classification Search ... 356/237.1–241.6, 356/426–431, 600–640
See application file for complete search history.

(56) References Cited

U.S. PATENT DOCUMENTS 5,857,474 A * 1/1999 Sakai et al. .............. 134/102.3

2005/0000545 A1 * 1/2005 Inagaki ......................... 134/18
2005/0227358 A1 * 10/2005 McEntee et al. ............... 436/5

FOREIGN PATENT DOCUMENTS

JP 9-186123 7/1997

* cited by examiner

*Primary Examiner*—L. G Lauchman
*Assistant Examiner*—Jarreas C Underwood
(74) *Attorney, Agent, or Firm*—Smith, Gambrell & Russell, LLP

(57) ABSTRACT

The present invention relates to a particle measuring method for irradiating light to a surface of a substrate to scatter the light so as to measure a condition of particles on the substrate based on the scattered light. The particle measuring method according to the present invention comprises the steps of: heating a certain liquid to obtain a steam; supplying the steam onto a substrate so that a content of the steam is absorbed by each particle, while a temperature of the substrate is maintained in such a manner that the steam does not condense on the substrate; cooling the substrate before the particle dries so that the content absorbed by the particle is solidified, while preventing generation of solidified substance on regions of the surface of the substrate to which no particle adheres; and irradiating light to the substrate to scatter the light and detecting the scattered light, under a condition in which the content absorbed by the particle has been solidified.

12 Claims, 8 Drawing Sheets

PARTICLE MEASURING METHOD AND PARTICLE MEASURING APPARATUS

FIELD OF THE INVENTION

The present invention relates to a particle measuring method and a particle measuring apparatus, for measuring a condition of particles adhering to a surface of a substrate.

BACKGROUND ART

In a semiconductor manufacturing apparatus, particles sometimes adhere to a substrate, which is caused by dusts from a driving part of a transfer system for the substrate, reaction products peeled from an inner wall of a processing vessel and/or a substrate stage, mists during a liquid process, and so on. Thus, in order to evaluate a performance, a processing condition, and an operating condition of a semiconductor manufacturing apparatus, a condition of particles adhering to a substrate, which has been processed in the semiconductor manufacturing apparatus, is inspected by means of a particle inspecting apparatus.

As shown in FIG. 9A, in the particle inspection apparatus, light such as a laser beam is irradiated to a substrate 100, and an intensity of scattered light scattered by particles 101 on the substrate 100 is measured. Thus, the number of particles 101, sizes thereof and so on are measured.

The smaller the size of a particle 101 is, the weaker the scattered light from the particle 101 becomes. In this case, detection of the scattered light becomes difficult. In addition, since the substrate 100 has been subjected to various processes, the substrate 100 may be slightly undulated, or may have some Irregularities on a surface thereof. In this case, as shown in FIG. 9B, since a laser beam is also scattered on the surface of the substrate 100, it is impossible to distinguish between the scattered light that has been scattered on the surface of the substrate 100 and the scattered light that has been scattered by the particles 101 (error of measurement is significantly serious). This phenomenon becomes more conspicuous when the particles 101 are smaller in size.

For these reasons, it has been difficult to accurately detect the particles 101 smaller than, e.g., 0.03 μm.

It has been proposed that an Intensity of a laser beam to be irradiated is Increased so as to increase an intensity of scattered light from the particle 101. However, irradiation of the laser beam of such an increased intensity (output) is disadvantageous in that some particles 101 may explode (burn) and disappear by receiving the energy of the laser beam, and thus the particles cannot be detected.

JP9-186123A (particularly sections 0041 to 0044) proposes a method in which a mist of water is supplied to a cooled substrate so as to form an ice on the substrate around a particle as a base point. According to this method, a seeming size of the particle can be enlarged. (Subsequently, by blowing a gas under a high pressure to the surface of the substrate, the surface of the substrate is cleaned.) However, the inventors of the present invention have found that this method is disadvantageous in that the ice is also formed on regions of the surface of the substrate to which no particle adheres, so that a seeming amount of particles may be undesirably increased.

On the other hand, in order to cope with more minute patterns for the substrate, there is an ongoing demand for more accurately grasping (obtaining) an adhering condition of particles 101 that are more minute.

SUMMARY OF THE INVENTION

The present invention has been made under these circumstances. The object of the present invention is to provide a particle measuring method and a particle measuring apparatus capable of accurately detecting particles of even smaller size, by irradiating light to a surface of a substrate to scatter the light thereon so as to measure a condition of the particles on the substrate based on the scattered light.

The present invention is a particle measuring method for irradiating light to a surface of a substrate to scatter the light so as to measure a condition of particles on the substrate based on the scattered light, the particle measuring method comprising the steps of: heating a certain liquid to obtain a steam; supplying the steam onto a substrate so that a content of the steam is absorbed by each particle, while a temperature of the substrate is maintained in such a manner that the steam does not condense on the substrate; cooling the substrate before the particle dries so that the content absorbed by the particle is solidified, while preventing generation of solidified substance on regions of the surface of the substrate to which no particle adheres; and irradiating light to the substrate to scatter the light and detecting the scattered light, under a condition in which the content absorbed by the particle has been solidified.

In this specification, to absorb the content of the steam (for example, a content of water vapor) does not mean that a droplet of water (liquid) adheres to the particle, but means that the particle is filled with the steam.

According to the present invention, when the light is irradiated on the surface of the substrate and scattered thereon so as to measure a condition of particles on the substrate based on the scattered light, a content of the steam of a liquid is absorbed by each particle, and the content absorbed by the particle is solidified, while preventing formation of solidified substance (for example, ice) on regions of the surface of the substrate to which no particle adheres (to be specific, a temperature of the atmosphere and/or a temperature of the substrate are adjusted). Thus, a seeming size of the particle can be effectively enlarged, whereby even when the particle is of a smaller size, such a particle can be accurately measured. At the same time, there is no possibility that ice on the regions free of particles is erroneously measured as a particle, since no ice is formed on such regions. Thus, it is possible to more accurately measure the number of particles and/or adhesion (presence) of particles.

Preferably, the step at which the content of the steam is absorbed by the particle is performed while the substrate is being heated.

In addition, preferably, a temperature of the steam to be supplied onto the substrate is higher than a temperature of the substrate.

In addition, preferably, a step of heating the substrate to remove a liquid on the substrate is performed, before the step at which the content of the steam is absorbed by the particle.

In addition, preferably, a step of heating the substrate to dry the particle is performed, after the step at which the scattered light is detected.

The present invention is a particle measuring apparatus that irradiates light to a surface of a substrate to scatter the light so as to measure a condition of particles based on the scattered light, the particle measuring apparatus comprising: a steam supply chamber that supplies a steam onto a substrate, the steam being obtained by heating a certain liquid, so that a content of the steam is absorbed by each particle, while a temperature of the substrate is maintained in such a manner that the steam does not condense on the substrate; a cooling chamber that forms an atmosphere in which the content absorbed by the particle is solidified, while preventing generation of solidified substance on regions of the surface of the substrate to which no particle adheres; a transfer unit that transfers the substrate from the steam supply chamber to the cooling chamber, before the content absorbed by the particle dries; and a particle measuring unit that irradiates light to the substrate to scatter the light, and detects the scattered light; wherein an atmosphere of an area through which the substrate passes while the substrate is transferred by the transfer unit is set in such a manner that the steam does not condense on the substrate, and an atmosphere in which the light is irradiated to the substrate by the particle measuring unit is set in such a manner that a solidified substance of the content absorbed by the particle does not melt.

According to the present invention, a seeming size of the particle can be effectively enlarged, whereby even when the particle is of a smaller size, such a particle can be accurately measured. At the same time, there is no possibility that ice on the regions free of particles is erroneously measured as a particle, since no ice is formed on such regions. Thus, it is possible to more accurately measure the number of particles and/or adhesion (presence) of particles.

For example, the particle measuring unit is disposed inside a measuring chamber that is separated from the cooling chamber, and the substrate that has been transferred to the cooling chamber is configured to be transferred to the measuring chamber.

Preferably, the steam supply chamber includes a heating unit for heating the substrate.

In addition, preferably, a temperature of the steam is set higher than a temperature of the substrate.

In addition, preferably, the steam supply chamber is configured to heat the substrate to remove a liquid on the substrate, before the steam supply chamber supplies the steam to the substrate.

In addition, preferably, the steam supply chamber is configured to heat the substrate to dry the particle, after the particle measuring unit detects the scattered light.

Further, the present invention is a storage medium storing a computer program used for a particle measuring apparatus that irradiates light to a surface of a substrate to scatter the light so as to measure a condition of particles on the substrate based on the scattered light, wherein the computer program incorporates commands for performing the particle measuring method having the above features.

BEST MODE FOR CARRYING OUT THE INVENTION

Figure 1:
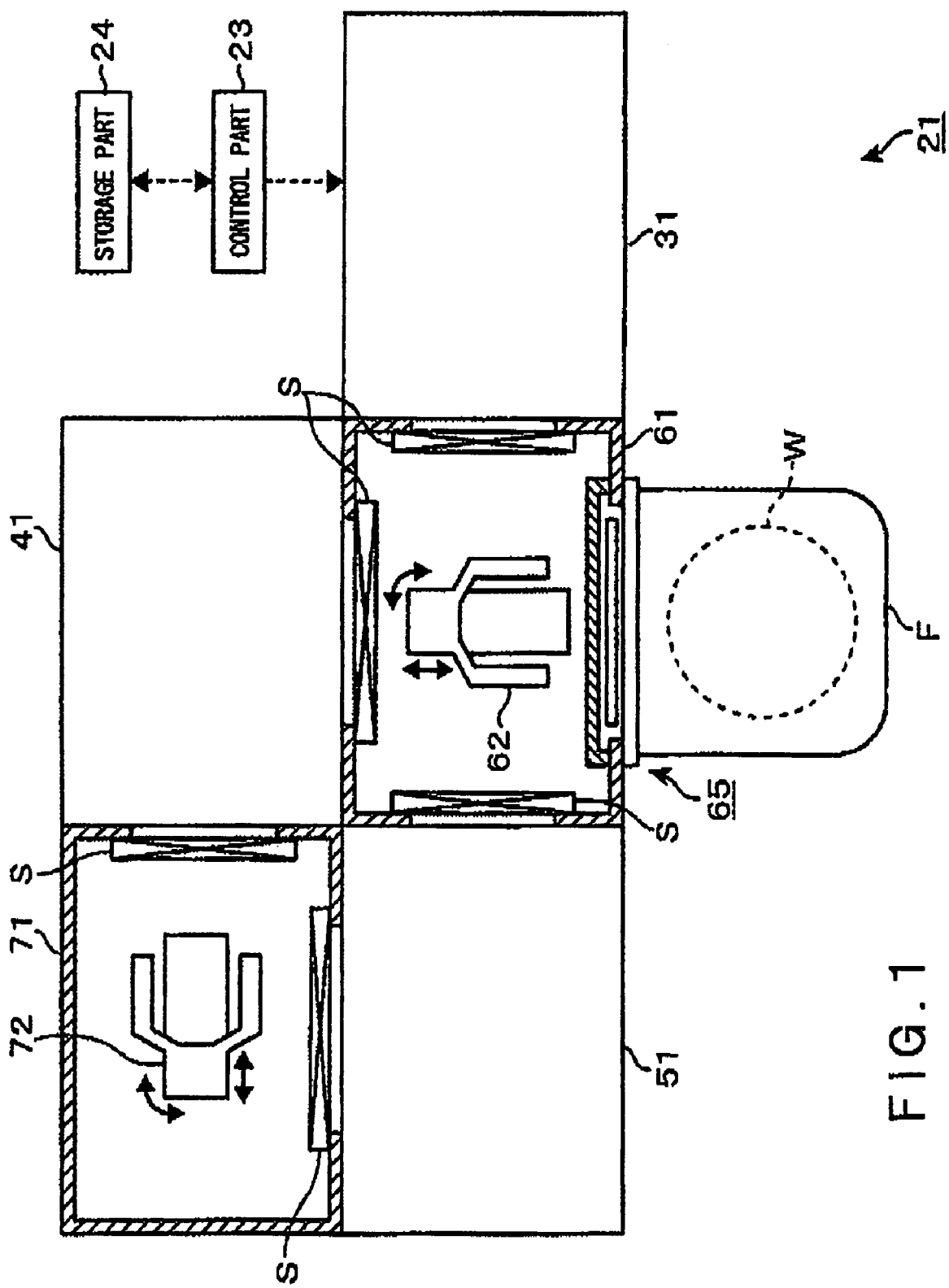
FIG. 1 is a plan view showing an embodiment of a particle measuring apparatus for carrying out a particle measuring method according to the present invention.

An embodiment of a particle measuring apparatus for carrying out a particle measuring method according to the present invention is described with reference to FIGS. 1 to 4. As shown in FIG. 1, a particle measuring apparatus 21 in this embodiment includes a steam supply chamber 31, a cooling chamber 41, and a particle measuring unit 51. The steam supply chamber 31, the cooling chamber 41, and the particle measuring unit 51 are connected to a first transfer chamber 61. Connected to the first transfer chamber 61 is a FOUP F as a sealable carrier in which a plurality of wafers W can be accommodated. In order to open and close a lid of the FOUP F, the first transfer chamber 61 is provided with an opening/closing mechanism 65. The cooling chamber 41 and the particle measuring unit 51 are connected to a second transfer chamber 71. The steam supply chamber 31, the cooling chamber 41, and the particle measuring unit 51 are configured to be respectively separated (isolated) from the first transfer chamber 61 and the second transfer chamber 71 by respective shutters S.

The first transfer chamber 61 and the second transfer chamber 71 are equipped with a first transfer unit 62 and a second transfer unit 72, respectively. The first transfer unit 62 and the second transfer unit 72 are configured to be horizontally movable and rotatable to transfer a wafer W while the corresponding shutters S are opened. The first transfer unit 62 is also configured to be vertically movable. In order to maintain a temperature of the wafer W at a constant level, each of the first transfer unit 62 and the second transfer unit 72 may be provided with a temperature adjusting unit. Specifically, the first transfer unit 62 may have a heating unit, while the second transfer unit 72 may have a cooling unit.

The particle measuring apparatus 21 is also provided with a control part 23 formed of a computer, for example. The control part 23 includes a data processing part formed of a program, a memory, and a CPU. The program incorporates commands for sending, for example, control signals from the control part 23 to respective members (elements) of the particle measuring apparatus 21 to cause the members to perform respective steps, which are described below, so as to subject a wafer W to a predetermined process or transfer. The memory has an area in which values of process parameters, such as a temperature of the wafer W, a holding period, a gas flowrate, a temperature of a heater for evaporating a purified water, are written. When the CPU executes the respective commands of the program, the values of these process parameters are read out, and control signals corresponding to the read-out values of the parameters are respectively sent to the members of the particle measuring apparatus 21.

Generally, the program (and possibly a program relating to an input operation and/or display of the processing parameters) is stored in a storage part 24 constituted by a computer storage medium such as a flexible disc, a compact disc, an MO (magnet optic disc), or a hard disc, and is installed in the control part 23.

Figure 2:
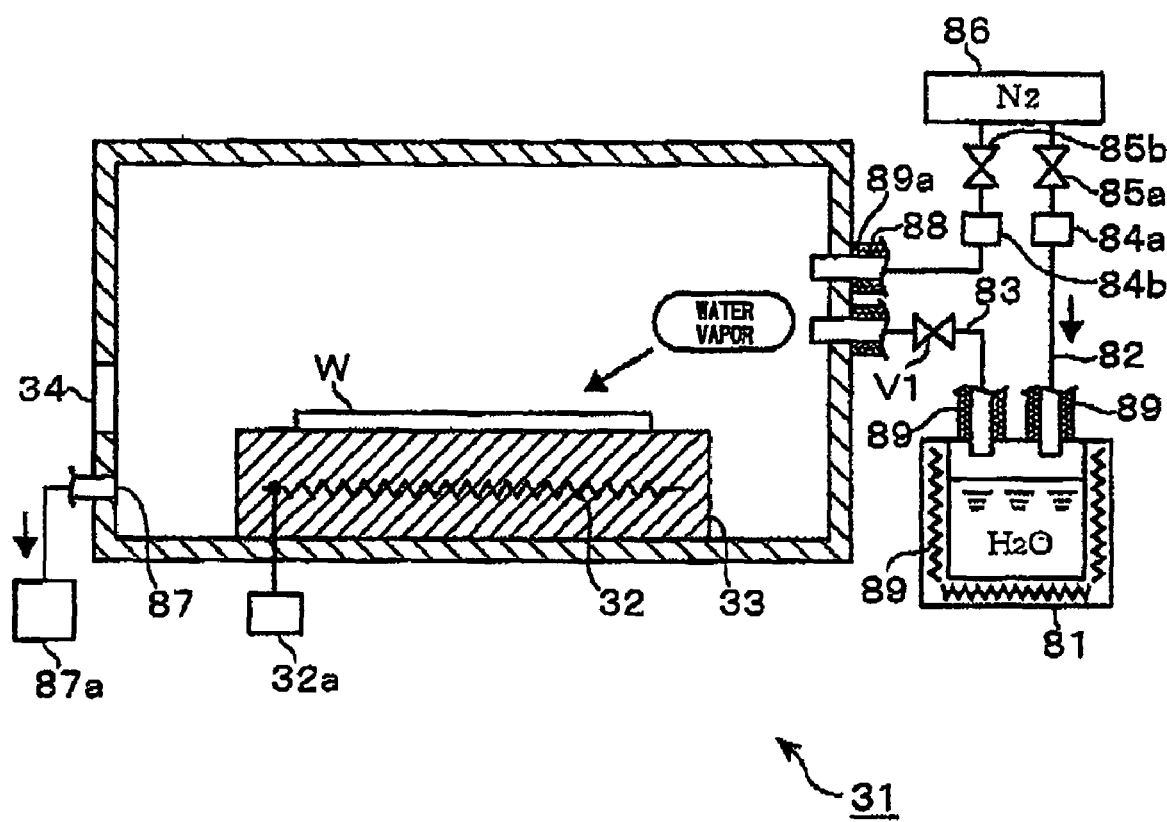
FIG. 2 is a longitudinal sectional view showing an example of a steam supply chamber of the particle measuring apparatus shown in FIG. 1.

Next, the steam supply chamber 31 is described. As shown in FIG. 2, in the steam supply chamber 31, there is disposed a stage 33 in which a heater 32 as a heating unit for heating a wafer W is embedded. The heater 32, which is connected to a power source 32a, is capable of heating a wafer W to about 80° C., for example. The stage 33 is equipped with an elevating unit such as a plurality of pins, not shown. A wafer W can be transferred between the stage 33 and the first transfer unit 62 by means of the elevating unit, via a transfer port 34 formed in a sidewall of the steam supply chamber 31. An exhaust port 87 is also opened in the sidewall of the steam supply chamber 31, whereby an atmosphere in the steam supply chamber 31 can be exhausted via the exhaust port 87 by an exhaust pump 87a.

Connected to another sidewall of the steam supply chamber 31 at a position opposed to the exhaust port 87 is one end of a steam supply path 83. The other end of the steam supply path 83 is connected, via a valve V1, to an upper wall of a reservoir 81 in which a liquid such as a purified water is reserved. A carrier-gas supply path 82 is also connected to the upper wall of the reservoir 81. To the carrier-gas supply path 82, there is connected, via a flowrate control part 84a and a valve 85a, a carrier-gas source 86 storing, for example, a nitrogen gas. The carrier-gas source 86 is also connected to the steam supply chamber 31 through a dry-gas supply path 88 via a valve 85b and a flowrate control part 84b. Thus, a nitrogen gas can be directly supplied to the steam supply chamber 31, without passing through the reservoir 81.

The carrier-gas supply path 82, the reservoir 81, and the steam supply path 83 are provided with a heating unit 89 such as a tape heater. Thus, a stable water steam having, e.g., a temperature of 90° C. and a relative humidity of 90%, can be supplied to the steam supply chamber 31. In addition, the dry-gas supply path 88 is provided with a heating unit 89a such as a tape heater. Thus, for example, it is possible to supply a dried nitrogen gas that has been heated at 90° C. into the steam supply chamber 31. Therefore, a water steam in the steam supply chamber 31 can be discharged through the exhaust port 87, without condensation (solidification) of the steam.

Figure 3:
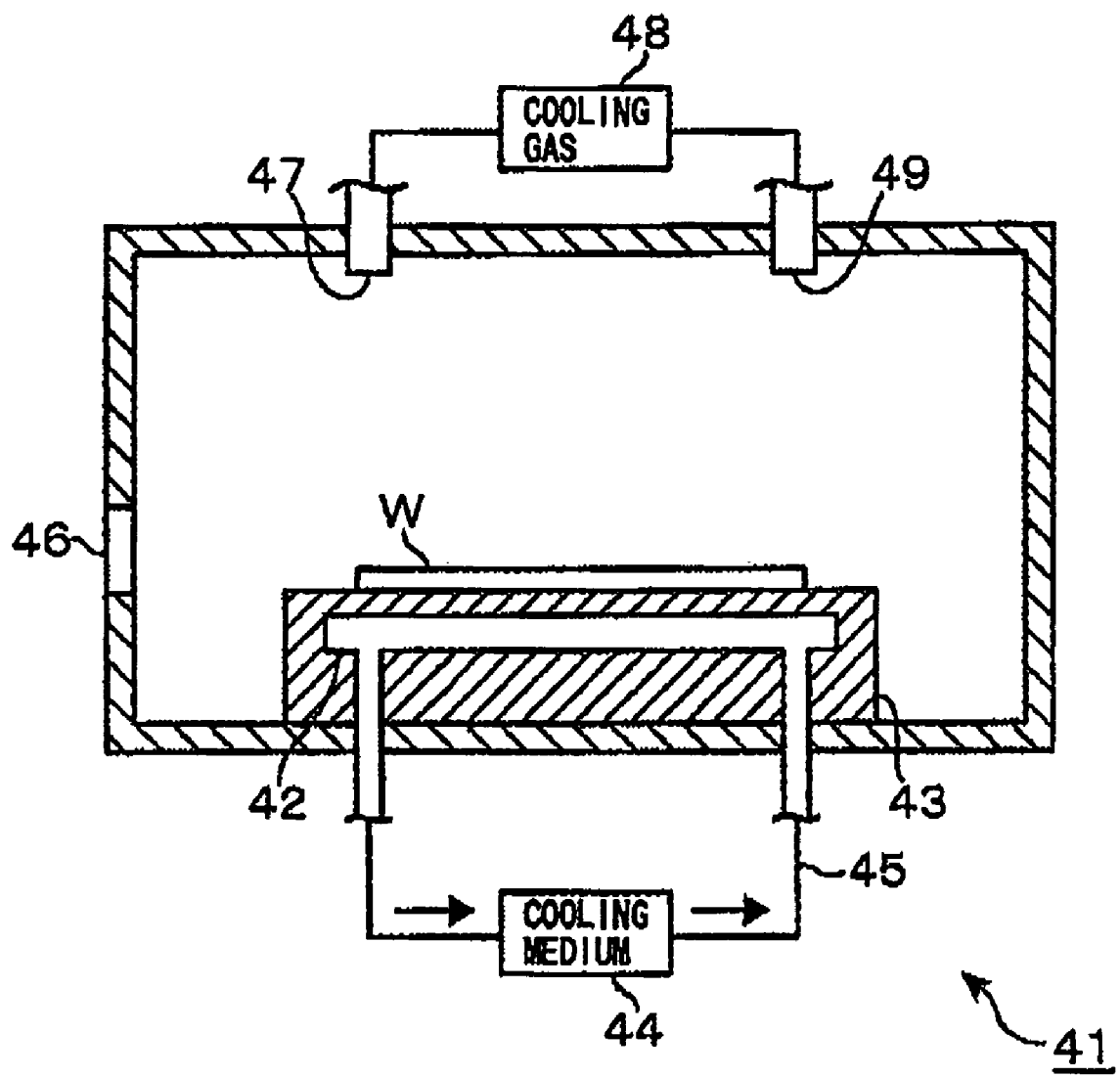
FIG. 3 is a longitudinal sectional view showing an example of a cooling chamber of the particle measuring apparatus shown in FIG. 1.

As shown in FIG. 3, a stage 43 is disposed in the cooling chamber 41. The stage 43 is equipped with, as a means for cooling the stage 43, a cooling-medium pool 42 in which a cooling medium such as a cooling gas is circulated. The cooling-medium pool 42 is connected to a cooling-medium source 44 through a circulation path 45, so that the cooling medium can be circulated through the cooling-medium pool 42 and the cooling-medium source 44. In order that a wafer W placed on the stage 43 can be cooled at a predetermined cooling speed of, e.g., 20° C./min, a temperature of the cooling medium is set (adjusted) to be, for example, −20° C. by another cooling means, not shown, disposed on the cooling-medium source 44.

A gas supply port 47 for supplying a cooling gas is formed in a ceiling wall of the cooling chamber 41. In addition, a gas outlet port 49 for discharging the cooling gas is formed in the ceiling wall of the cooling chamber 41. A cooling gas in a cooling-gas source 48, e.g. a nitrogen gas cooled at −21° C., can be supplied from the gas supply port 47, and discharged from the gas outlet port 49. The circulation of the cooling gas allows a temperature in the cooling chamber 41 to be maintained at less than 20° C. Although the cooling-gas source 48 constitutes a part of the cooling unit in the present invention, the cooling-gas source 48 can be omitted, when a thickness of a wafer W is so thin that a water content of the particle 10 can be frozen only by the cooling of the cooling-medium pool 42 disposed in the stage 43.

In addition, the stage 43 has an elevating unit, not shown, whereby a wafer W can be transferred between the stage 43 and the first transfer unit 62 or the second transfer unit 72 via a transfer port 46 formed in a sidewall of the cooling chamber 41.

Figure 4:
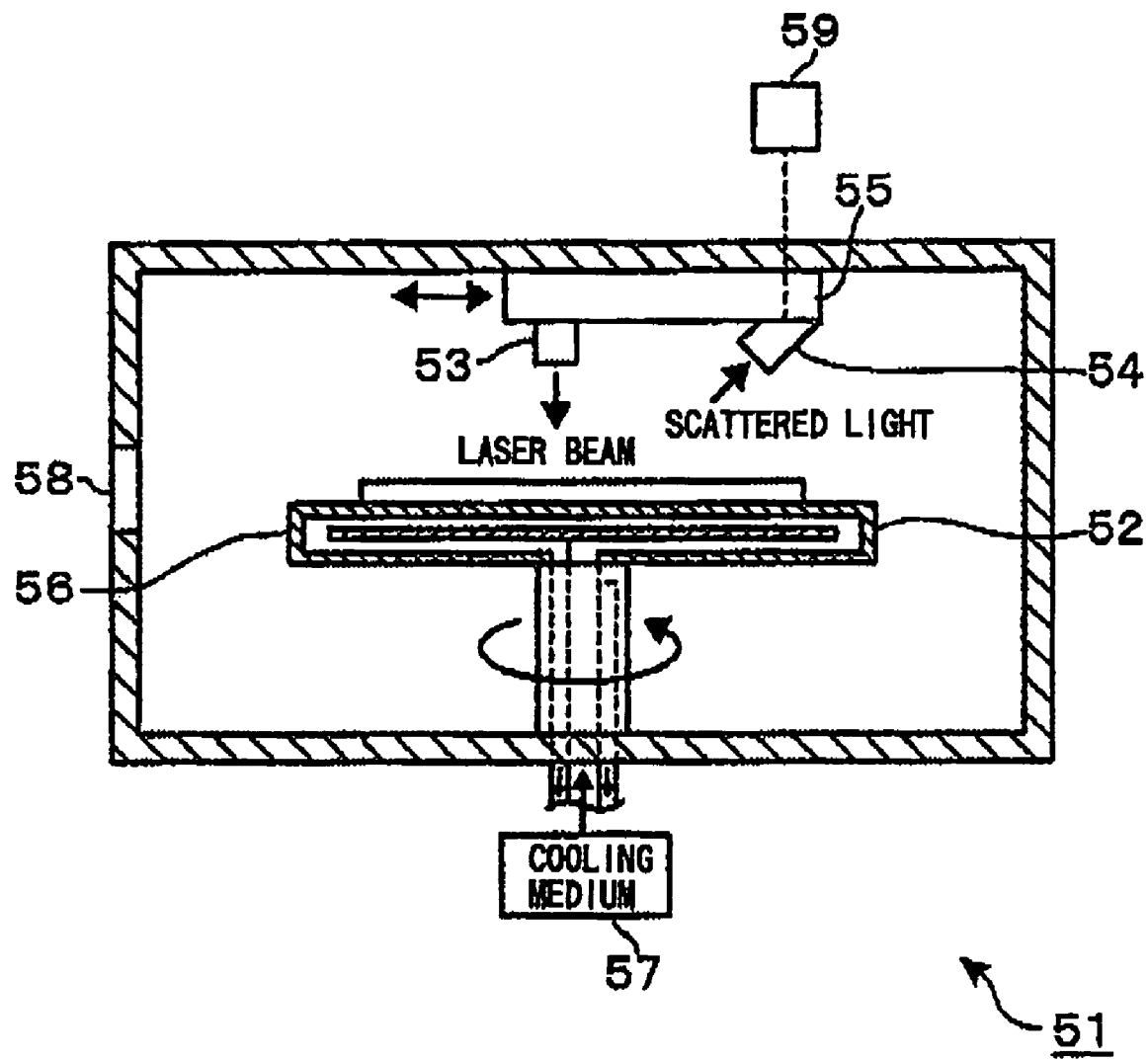
FIG. 4 is a longitudinal sectional view showing an example of a particle measuring unit of the particle measuring apparatus shown in FIG. 1.
Figure 5:
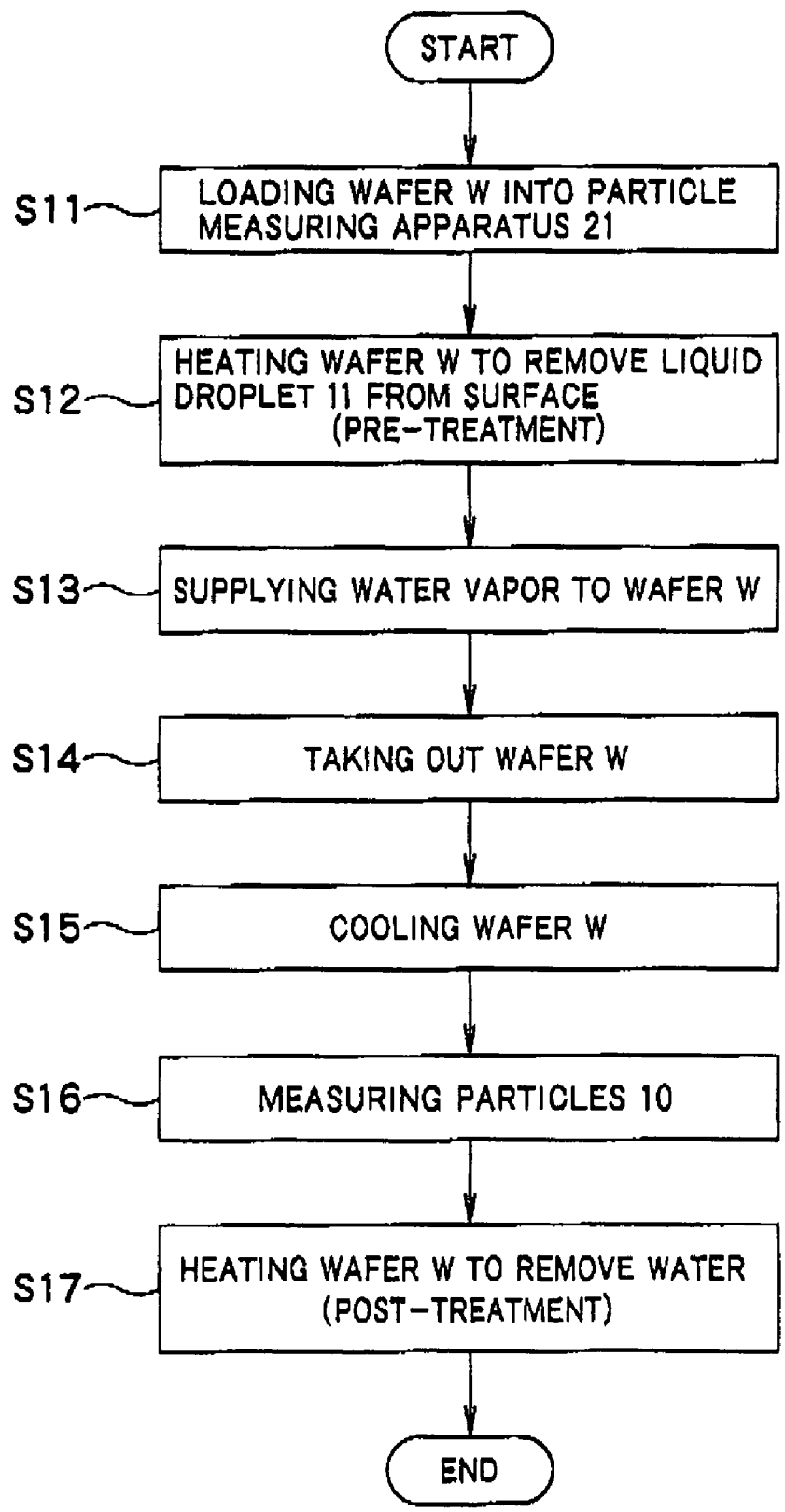
FIG. 5 is a flowchart showing an embodiment of the particle measuring method according to the present invention.

As shown in FIG. 4, the particle measuring unit 51, which forms a measuring chamber, includes a rotatable table 52 and a particle measuring unit 55. The particle measuring unit 55 has a light irradiating part 53 for irradiating light such as a laser beam to a wafer W, and a light receiving part 54 for receiving the light after scattered by particles 10 on the wafer W. The particle measuring unit 55 is configured to be movable such that a surface of a wafer W is continuously scanned in a radial direction thereof by the laser beam irradiated from the light irradiating part 53. In addition, the particle measuring unit 55 is connected to a signal processing part 59 that processes a signal based on the light received by the light receiving part 54.

In order that a wafer W is cooled at, e.g., −5° C. to maintain a solidified condition of the water content of each particle 10 (to prevent an ice formed in the particle 10 and an ice formed around the particle 10 from melting), a cooling-medium path 56 as a cooling means is disposed in the table 52. The cooling-medium path 56 is connected to a cooling-medium source 57, so that a cooling medium such as a cooling gas can be circulated through the cooling-medium path 56.

The table 52 has an elevating unit, not shown, whereby a wafer W can be transferred between the table 52 and the first transfer unit 62 or the second transfer unit 72 via a transfer port 58 formed in a sidewall of the particle measuring unit 51.

Figure 6:
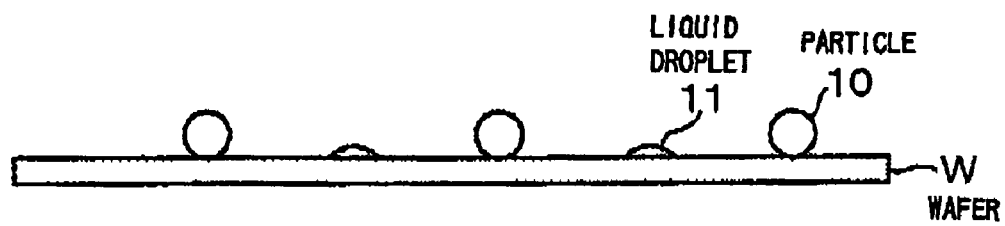
FIG. 6 is a side view of a wafer W which is subjected to a particle measurement.

Next, an embodiment of the particle measuring method according to the present invention is described with reference to FIGS. 5 to 8. The following description is made on the assumption that a wafer W, to which the particle measuring method in this embodiment is applied, has been subjected to various processes by a substrate processing apparatus, not shown, and that particles 10 as shown in FIG. 6 adhere to a surface of the wafer W. Further, there may be a case in which minute liquid droplets 11 of an organic solvent and/or water adhere to the wafer W because of various processes and/or a cleaning process. Although FIG. 6 illustrates the particle 10 having a simple shape, the particle 10 actually has a complicated shape with a larger surface area.

(Step S11: Step of Loading Wafer W)

At first, the FOUP F accommodating a plurality of wafers W is connected to the particle measuring apparatus 21. Then, a wafer W to be subjected to the measurement of particles 10 is loaded from the FOUP F into the particle measuring apparatus 21 by the first transfer unit 62.

(Step S12: Pre-treatment Step)

Figure 7A:
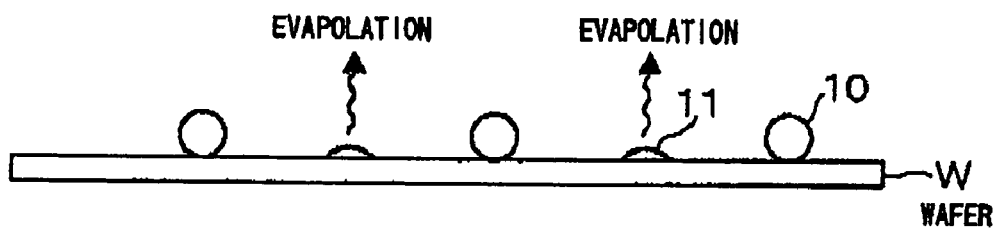
FIGS. 7A to 7C and FIGS. 8A to 8C are side views of the wafer W corresponding to the respective steps in the course for measuring particles.
Figure 7B:

Then, the wafer W is placed on the stage 33 in the steam supply chamber 31. Then, a temperature of the wafer W is heated up to 80° C. by the heater 32, and the wafer W is held for some tens seconds in this heated condition. Due to this pre-treatment, as shown in FIG. 7A, the liquid droplets 11 are evaporated (volatilized), and thus, as shown in FIG. 7B, only the particles 10 remain on the surface of the wafer W. This process step is performed in order that the liquid droplets 11 are not measured as the particles 10 at the following step S16 for measuring the particles 10. If the liquid droplets 11 are measured as the particles 10, a condition of the particles 10 caused by dusts from a driving mechanism or the like and/or reaction products, which should be actually measured, cannot be accurately measured, resulting in inaccurate evaluation of a performance and/or an operating condition of the apparatus. In order to avoid this, the particles 10 and substances other than the particles 10, such as the liquid droplets 11, are "separated" from each other.

(Step S13: Steam Supplying Step)

Figure 7C:
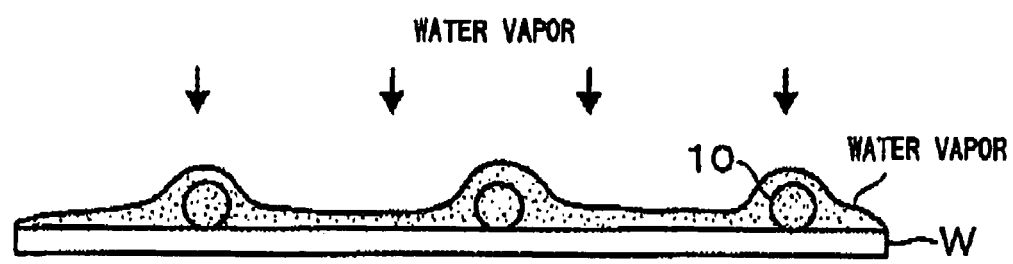

A water steam of, e.g., 90° C., which temperature is higher than the temperature of the wafer W, is supplied, together with a carrier gas such as a nitrogen gas, onto the wafer W that has been still heated, over a predetermined period of time. To be specific, a water vapor having a temperature of 90° C. and a relative humidity of 90% is supplied onto the wafer W, with the carrier-gas supply path 82, the reservoir 81, and the steam supply path 83 being heated by the heating unit 89. Simultaneously therewith, an atmosphere in the steam supply chamber 31 is exhausted by the exhaust pump 87a. Thus, a steam pressure (vapor pressure) of water in the steam supply chamber 31 is gradually increased, and the steam supply chamber 31 is finally filled with the water steam. Due to this step, as shown in FIG. 7C, the surface of the wafer W is covered with the steam, and a certain content of the steam is absorbed by the particles 10.

In order to increase the steam pressure (to increase an amount of steam in the carrier gas), a temperature of the steam is set relatively higher. In addition, in order that the steam pressure is almost saturated near the wafer W so as to facilitate the particles 10 to absorb the water content of the steam, the temperature of the steam is set higher than the temperature of the wafer W. However, the temperature of the steam and the temperature of the wafer W are adjusted such that the steam does not condense on regions of the surface of the wafer W on which no particle 10 rests.

The above steam is of course a gas, and thus cannot be practically observed. Moreover, not only around the wafer W and the particles 10, but also the overall atmosphere in the steam supply chamber 31 is filled with the steam. However, with a view to facilitating understanding, FIG. 7C particularly illustrates the steam near the wafer W. Herein, absorption of water content of the steam does not mean that mist of water (liquid droplets) adheres to the particles, but means that the particles are filled with the steam. In other words, as compared with an atmosphere under a normal temperature and a normal pressure, the steam pressure is increased in an atmosphere where the wafer W is placed.

(Step S14: Step of Taking out Wafer W)

Thereafter, the wafer W in the steam supply chamber 31 charged with the above steam atmosphere is taken out therefrom into the first transfer chamber 61 having an atmosphere under a normal temperature and a normal pressure. At this time, a slight amount of the steam may flow from the steam supply chamber 31 into the first transfer chamber 61, or a slight amount of the steam may adhere to the first transfer unit 62. However, since the inside of the first transfer chamber 61 is adjusted by an airflow generating means, not shown, such that a steam pressure of water is lowered (to a normal pressure), the wafer W can be taken out without any condensation of the steam.

Since the wafer W was heated at the step S13, the temperature of the wafer W is higher than a temperature of the atmosphere in the first transfer chamber 61. Thus, the wafer W is cooled by the atmosphere surrounding the same in the first transfer chamber 61. At this time, the temperature of the wafer W is lowered more slowly than the temperature of the particle 10, because of the larger volume and the larger heat capacity of the wafer W than those of the particle 10 on the surface of the wafer W. Namely, the temperature of the particle 10 on the surface of the wafer W is lowered more quickly than the temperature of the wafer W.

Figure 8A:
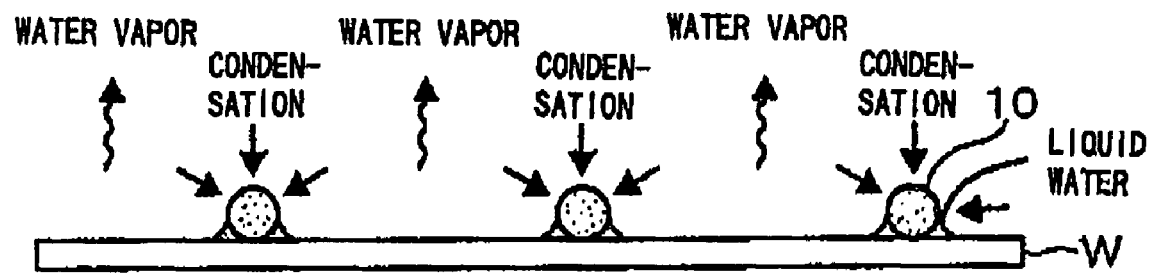

At this step where the wafer W is taken out to the atmosphere under a normal temperature and a normal pressure (in the first transfer chamber 61), both the wafer W and the particles 10 have already absorbed the water content of the steam (the wafer W and the particles 10 are filled with the steam). Herein, as described above, the cooling speeds of the wafer W and the particle 10 differ from each other. Thus, as shown in FIG. 8A, on the surface of the wafer W, the steam diffuses from the surface to the atmosphere of a lower steam pressure in the first transfer chamber 61, while in the particle 10 and around the particle 10 (a part in contact with the particle 10), the steam pressure of water is supersaturated, and thus the steam is condensed. That is, since the wafer W is slowly cooled, the steam on the surface of the wafer W can diffuse to the atmosphere in the first transfer chamber 61, before the steam pressure is saturated. On the other hand, since the particle 10 is quickly cooled, the water content of the particle 10 (water content in the particle 10 and around the particle 10) is condensed into a liquid water. In addition, in the particle 10 and around the particle 10, a surface area of the steam exposed to the atmosphere in the first transfer chamber 61 is relatively smaller, i.e., the steam entering a gap between the particle 10 and the wafer W and the steam entering the inside of the particle 10 are difficult to diffuse. Thus, such a steam is more likely to condense. The water content of the particle 10 that has been condensed into a liquid water is drawn to the particle 10 by a surface tension, so that a surface area thereof is reduced. Thus, the liquid water becomes difficult to evaporate, as compared with the steam on the surface of the wafer W.

Meanwhile, after the wafer W is unloaded from the steam supply chamber 31, the shutter S is closed, and the valve V1 and the valve 85a are closed. Then, a nitrogen gas is supplied through the dry-gas supply path 88 into the steam supply chamber 31, so that the steam therein is discharged.

(Step S15: Step of Cooling Wafer W)

Figure 8B:
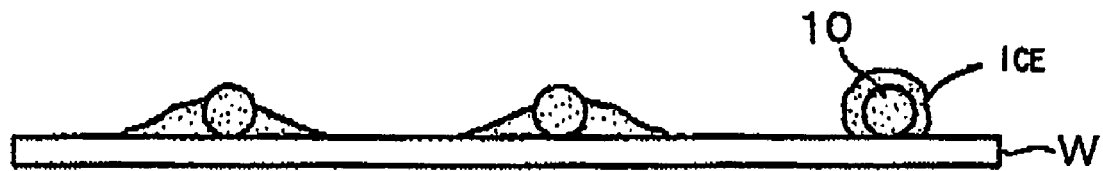

Then, the wafer W is loaded into the cooling chamber 41. In the cooling chamber 41, a temperature of the stage 43 and a temperature of an atmosphere in the chamber are set in such a manner that a surface temperature of the wafer W, which is placed on the stage 43, is lowered to a temperature at which the water content of the particle 10 can be sufficiently frozen, e.g., −10° C., at an average temperature lowering speed of, e.g., 20° C./min. The wafer W is loaded into the cooling chamber 41 through an atmosphere which is adjusted such that the water content does not condense on the regions of the wafer W other than the particles 10. However, even if there is a possibility that the water content condenses, there is no problem as long as the temperatures of the stage 43 and the in-chamber atmosphere and/or the average temperature lowering speed is set such that the condensed water content does not freeze but evaporates, but that the water content of the particle 10 freezes. In order to fulfill these conditions, it is important to prepare data useful therefor based on experiments. In this manner, as shown in FIG. 8B, the water content of each particle 10 is frozen, and the seeming size of the particle 10 is enlarged. Namely, the size of the particle 10 can be enlarged, without increasing the number of solidified substances on the wafer W.

(Step S16: Step of Measuring Particles 10)

Figure 8C:
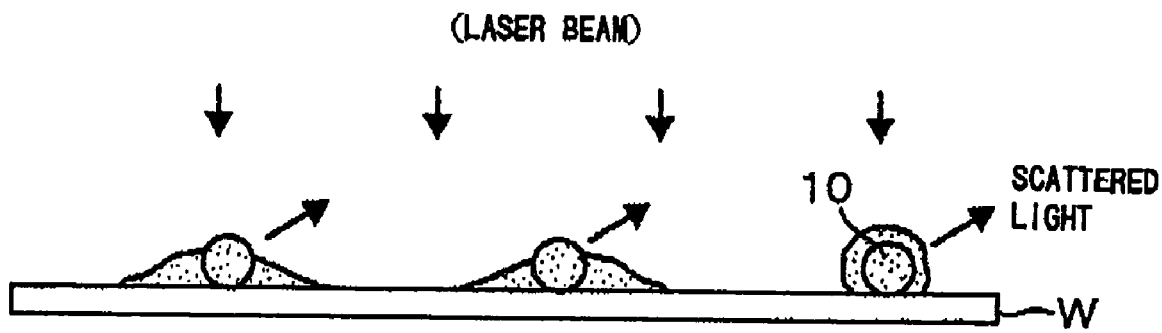
Figure 9A:
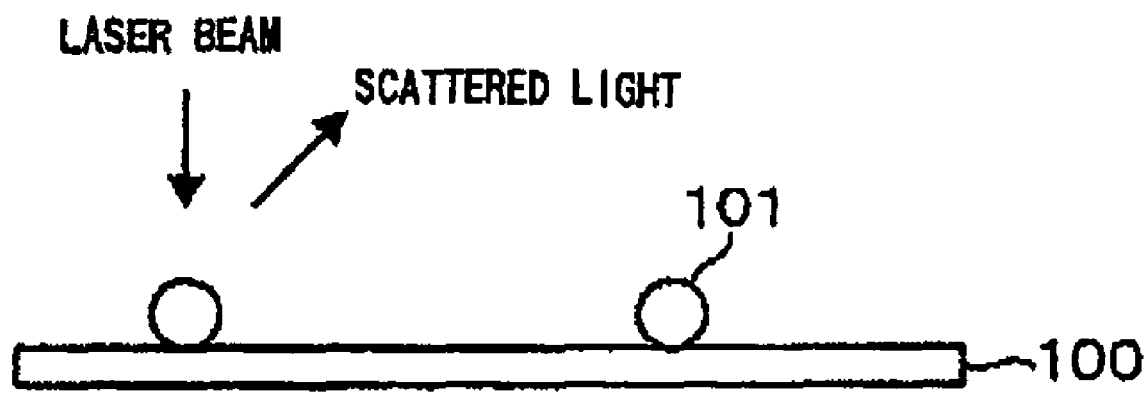
FIG. 9A is a side view for explaining a conventional particle measuring method.
Figure 9B:
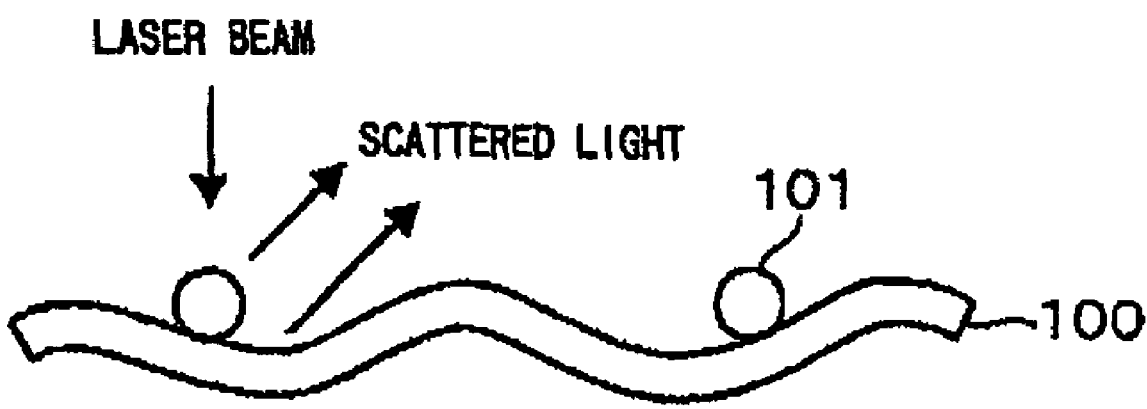
FIG. 9B is a side view for explaining a disadvantage of the method shown in FIG. 9A.

Then, the wafer W is loaded into the particle measuring unit 51. At this time, the wafer W is kept cooled (the water content of the particle 10 is kept solidified (condensed)), in order that the size of the particle 10, which was seemingly enlarged at the step S15, does not return to the original size. Thereafter, as shown in FIG. 8C, a laser beam is irradiated to the surface of the wafer W, and light scattered by the particles 10 is detected. Thus, the particles 10 are measured. Specifically, after the wafer W is placed on the table 52 whose temperature has been set at, e.g., −5° C., the table 52 is rotated. Then, while the table 52 is being rotated, the laser beam is irradiated from the light irradiating part 53 to the wafer W, scanned from a center of the wafer W toward a periphery thereof, for example, and the laser beam(s) scattered on the surface of the wafer W is received by the light receiving part 54. Then, the received-light signals are processed by the signal processing part 59. Based on the processing result, there can be obtained data relating to, e.g., the sizes and the number of the particles 10. During this measurement of the particles 10, the temperature of the particle 10 on the surface of the wafer W may be more or less increased by the laser beam. However, since the wafer W is sufficiently cooled by the cooling medium passing through the cooling-medium path 56, melting of the ice (solidified substance) on the wafer W can be prevented.

At this measurement step, since the particle 10 is surrounded by the ice so that the size of the particle 10 is enlarged, the laser beam can be easily scattered by the particle 10. Thus, even when the wafer W is slightly warped or has some irregularities, the laser beam(s) scattered by the particle 10 can be readily separated from noises such as laser beam(s) scattered by the wafer W itself. As a result, detection of particles 10 can be accurately performed.

(Step S17: Post-treatment Step)

After the particles 10 are measured, the wafer W is returned to the FOUP F. At this time, if the ice is melt, the atmosphere surrounding the wafer W in the FOUP F may possibly be contaminated by the water steam. Thus, preferably, the wafer W is again loaded into the steam supply chamber 31, the wafer W is heated at, e.g., 90° C. so as to dry the particles 10, and thereafter, the wafer W is returned to the FOUP F.

Following thereto, another wafer W for measuring particles 10, which is determined at predetermined intervals among product wafers W, is taken out from the FOUP F, and the measurement of particles 10 is performed in accordance with the same steps as described above.

According to the above embodiment, after the water content of the steam is absorbed by each of the particles 10 while the steam is prevented from being condensed on the surface of the wafer W, the wafer W is cooled, before the particle 10 dries, such that the water content of the particle 10 turns into ice, while preventing generation of ice on the regions of the wafer W to which no particle adheres, whereby the seeming size of the particle 10 is enlarged. That is, the seeming size of the particle 10 is enlarged without changing the number of solid bodies (solidified substances) on the wafer W. Therefore, it is possible to measure a condition of the particles 10 (to detect the number of particles 10 for each size, and/or presence thereof), while suppressing an influence from a surface condition (irregularities and/or warp) of the wafer W. Namely, an accurate measurement of the particles 10 can be achieved.

Further, before the steam is supplied to the wafer W, the wafer W is heated beforehand so as to remove a water and/or a volatile substance other than the particles 10. Thus, when the wafer W is cooled at the following step, formation of ice on substances other than the particles 10 can be prevented. Thus, increase in number of the solid bodies on the wafer W can be restrained, whereby the number of the particles 10 can be accurately measured.

Furthermore, at the steps S13 to S15, by controlling the size of the ice solidified around the particle 10 as a base point, i.e., by controlling an amount of steam to be supplied to the wafer W and/or cooling period of the wafer W, the size of the particle 10 can be adjusted. Thus, the size of the particle 10 to be detected (the size of the particle 10 that is not yet frozen) can be adjusted. Therefore, the number of particles 10 of desired size can be measured. In addition, the pre-treatment step (step S12) and/or the post-treatment step (step S17) may be omitted.

In the above embodiment, the cooling chamber 41 and the particle measuring unit 51 are separately installed. However, by making rotatable the stage 43 of the cooling chamber 41, and by providing the particle measuring unit 55 in the cooling chamber 41, the cooling chamber 41 and the particle measuring unit 51 may be unified. Alternatively, the cooling chamber 41 and the steam supply chamber 31 may be unified.

Further, when the water content of the steam is absorbed by the particles 10, the wafer W is heated in order that the steam does not condense on the wafer W. However, in place of this adjustment of the temperature of the wafer W, it is possible to adjust an amount of steam contained in a carrier gas to be supplied to the wafer W. Alternatively, it is possible to adjust both the temperature of the wafer W and the amount of steam.

Furthermore, in the above embodiment, although the water is used as a liquid, alcohol or the like may be used. In this case, a heating temperature of the wafer W in the steam supply chamber 31 is set at, e.g., about 20° C. to 80° C., and a cooling temperature of the wafer W in the cooling chamber 41 is set at, e.g., about 40° C. In this case, the terms "water content" and "ice" used in the above description are respectively construed as "component content" and "solidified substance".

The invention claimed is:

1. A particle measuring method for irradiating light to a surface of a substrate to scatter the light so as to measure a condition of particles on the substrate based on the scattered light, the particle measuring method comprising the steps of:
heating a certain liquid to obtain a steam;
supplying the steam onto a substrate so that a content of the steam is absorbed by each particle, while a temperature of the substrate is maintained in such a manner that the steam does not condense on the substrate;
cooling the substrate before the particle dries so that the content absorbed by the particle is solidified, while preventing generation of solidified substance on regions of the surface of the substrate to which no particle adheres; and
irradiating light to the substrate to scatter the light and detecting the scattered light, under a condition in which the content absorbed by the particle has been solidified.

2. The particle measuring method according to claim 1, wherein
the step at which the content of the steam is absorbed by the particle is performed while the substrate is being heated.

3. The particle measuring method according to claim 1, wherein
a temperature of the steam to be supplied onto the substrate is higher than a temperature of the substrate.

4. The particle measuring method according to claim 1, wherein
a step of heating the substrate to remove a liquid on the substrate is performed, before the step at which the content of the steam is absorbed by the particle.

5. The particle measuring method according to claim 1, wherein
a step of heating the substrate to dry the particle is performed, after the step at which the scattered light is detected.

6. A particle measuring apparatus that irradiates light to a surface of a substrate to scatter the light so as to measure a condition of particles based on the scattered light, the particle measuring apparatus comprising:
a steam supply chamber that supplies a steam onto a substrate, the steam being obtained by heating a certain liquid, so that a content of the steam is absorbed by each particle, while a temperature of the substrate is maintained in such a manner that the steam does not condense on the substrate;

a cooling chamber that forms an atmosphere in which the content absorbed by the particle is solidified, while preventing generation of solidified substance on regions of the surface of the substrate to which no particle adheres;

a transfer unit that transfers the substrate from the steam supply chamber to the cooling chamber, before the content absorbed by the particle dries; and a particle measuring unit that irradiates light to the substrate to scatter the light, and detects the scattered light;

wherein an atmosphere of an area through which the substrate passes while the substrate is transferred by the transfer unit is set in such a manner that the steam does not condense on the substrate, and an atmosphere in which the light is irradiated to the substrate by the particle measuring unit is set in such a manner that a solidified substance of the content absorbed by the particle does not melt.

7. The particle measuring apparatus according to claim 6, wherein the particle measuring unit is disposed inside a measuring chamber that is separated from the cooling chamber, and the substrate that has been transferred to the cooling chamber is configured to be transferred to the measuring chamber.

8. The particle measuring apparatus according to claim 6, wherein the steam supply chamber includes a heating unit for heating the substrate.

9. The particle measuring apparatus according to claim 6, wherein a temperature of the steam is set higher than a temperature of the substrate.

10. The particle measuring apparatus according to claim 6, wherein the steam supply chamber is configured to heat the substrate to remove a liquid on the substrate, before the steam supply chamber supplies the steam to the substrate.

11. The particle measuring apparatus according to claim 6, wherein the steam supply chamber is configured to heat the substrate to dry the particle, after the particle measuring unit detects the scattered light.

12. A storage medium storing a computer program used for a particle measuring apparatus that irradiates light to a surface of a substrate to scatter the light so as to measure a condition of particles on the substrate based on the scattered light, wherein the computer program incorporates commands for performing the particle measuring method according to claim 1.

* * * * *